(12) United States Patent
Kim

(10) Patent No.: US 9,719,126 B2
(45) Date of Patent: Aug. 1, 2017

(54) APPARATUS AND METHOD FOR PROCESSING A SAMPLE USING MICROWAVE

(75) Inventor: Yang Sun Kim, Seongnam-si (KR)

(73) Assignee: ASTA CO., LTD., Suwon-si, Gyeonggi-do (KR)

( * ) Notice: Subject to any disclaimer, the term of this patent is extended or adjusted under 35 U.S.C. 154(b) by 0 days.

(21) Appl. No.: 14/366,906

(22) PCT Filed: Aug. 23, 2012

(86) PCT No.: PCT/KR2012/006695
§ 371 (c)(1),
(2), (4) Date: Jul. 1, 2014

(87) PCT Pub. No.: WO2013/094843
PCT Pub. Date: Jun. 27, 2013

(65) Prior Publication Data
US 2014/0370534 A1    Dec. 18, 2014

(30) Foreign Application Priority Data

Dec. 22, 2011    (KR) .................. 10-2011-0139922

(51) Int. Cl.
*C12Q 1/34*    (2006.01)
*G01N 1/44*    (2006.01)
(Continued)

(52) U.S. Cl.
CPC ............. *C12Q 1/34* (2013.01); *G01N 1/44* (2013.01); *B01J 19/126* (2013.01);
(Continued)

(58) Field of Classification Search
CPC ............ A61B 18/1815; H01J 37/32192; B01J 19/126; B01J 2219/1209; H05B 6/6408; B01L 2300/1866; B01L 7/00
(Continued)

(56) References Cited

U.S. PATENT DOCUMENTS 4,915,880 A * 4/1990 Jenkins ............. B01F 15/00824
215/371
5,302,347 A * 4/1994 Van Den Berg et al. ...... 422/67
(Continued)

FOREIGN PATENT DOCUMENTS

JP    08-136422 A    5/1996
JP    2005-268624 A    9/2005
(Continued)

OTHER PUBLICATIONS

PCT International Search Report and Written Opinion, PCT/KR2012/006695, Feb. 7, 2013, 6 Pages.

*Primary Examiner* — Dennis M White
*Assistant Examiner* — Bryan Kilpatrick
(74) *Attorney, Agent, or Firm* — Fenwick & West LLP

(57) ABSTRACT

An apparatus for processing a sample using microwaves comprises: a reaction vessel comprising a chamber which accommodates a refrigerant and a sample and an injection port through which a gas is injected; a microwave source which irradiates microwaves into the chamber; a connector which carries the gas injected through the injection port; and a gas supplier which is located in the chamber and injects the gas carried by the connector to a refrigerant in the chamber. The connector may comprise a gas carrying portion located above the level of the refrigerant in the chamber.

8 Claims, 11 Drawing Sheets

(51) Int. Cl.
*G01N 1/40* (2006.01)
*B01L 7/00* (2006.01)
*B01J 19/12* (2006.01)

(52) U.S. Cl.
CPC .......... *B01J 2219/1209* (2013.01); *B01L 7/00* (2013.01); *B01L 2300/1866* (2013.01); *G01N 1/4044* (2013.01)

(58) Field of Classification Search
USPC ............... 118/723 W; 607/101, 102; 422/21; 219/678; 436/94; 435/18, 287.1
See application file for complete search history.

(56) References Cited

U.S. PATENT DOCUMENTS

| | | | | |
|---|---|---|---|---|
| 5,830,417 | A | * | 11/1998 | Kingston .................. 422/186.29 |
| 6,676,905 | B2 | | 1/2004 | Al-Obeidi et al. |
| 6,992,759 | B2 | * | 1/2006 | Nakayama ......... G01N 21/0303 |
| | | | | 250/339.07 |
| 7,392,718 | B2 | | 7/2008 | Emoto |
| 2006/0107769 | A1 | * | 5/2006 | Emoto ....................... 73/863.11 |

FOREIGN PATENT DOCUMENTS

| | | |
|---|---|---|
| JP | 2006-136207 A | 6/2006 |
| KR | 10-2004-0012902 A | 2/2004 |
| KR | 10-2005-0042415 A | 5/2005 |
| KR | 10-2009-0110599 A | 10/2009 |

* cited by examiner

[Fig. 1]
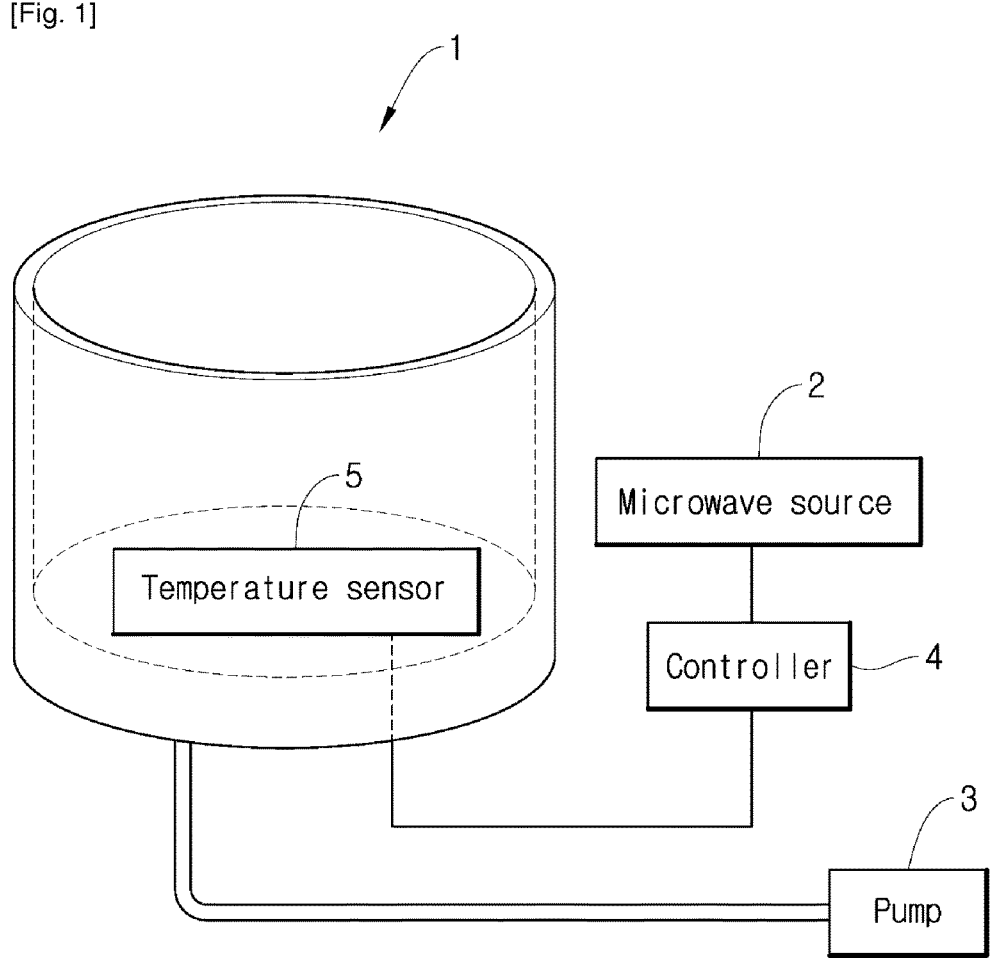
[Fig. 2]
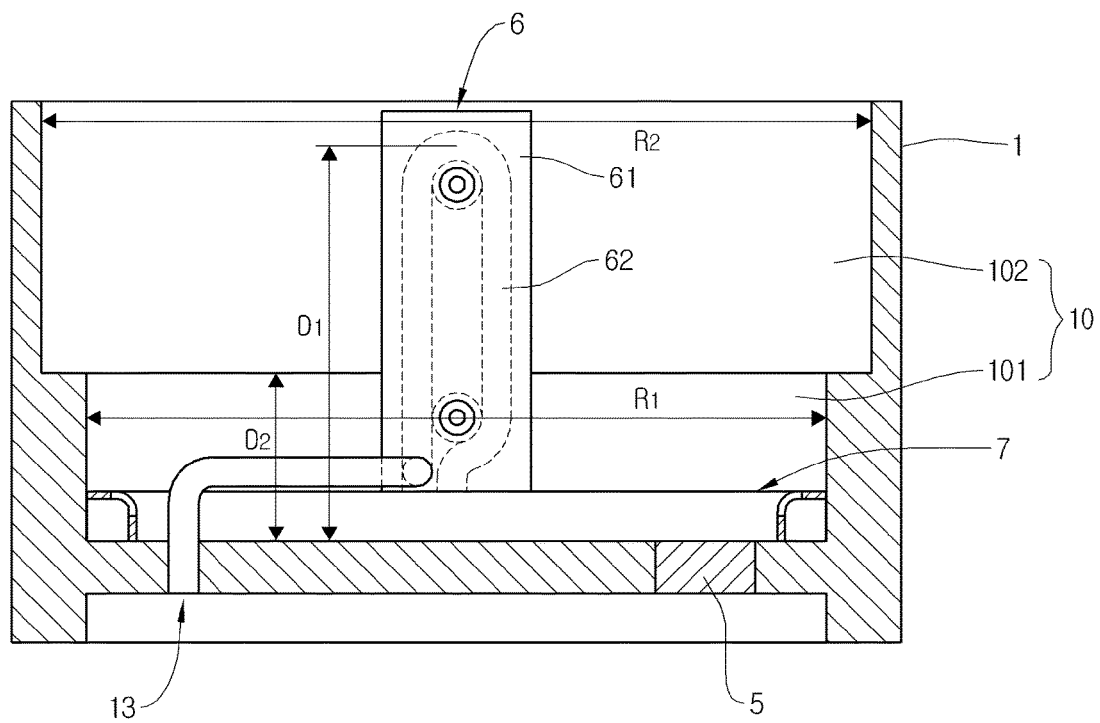

[Fig. 3]
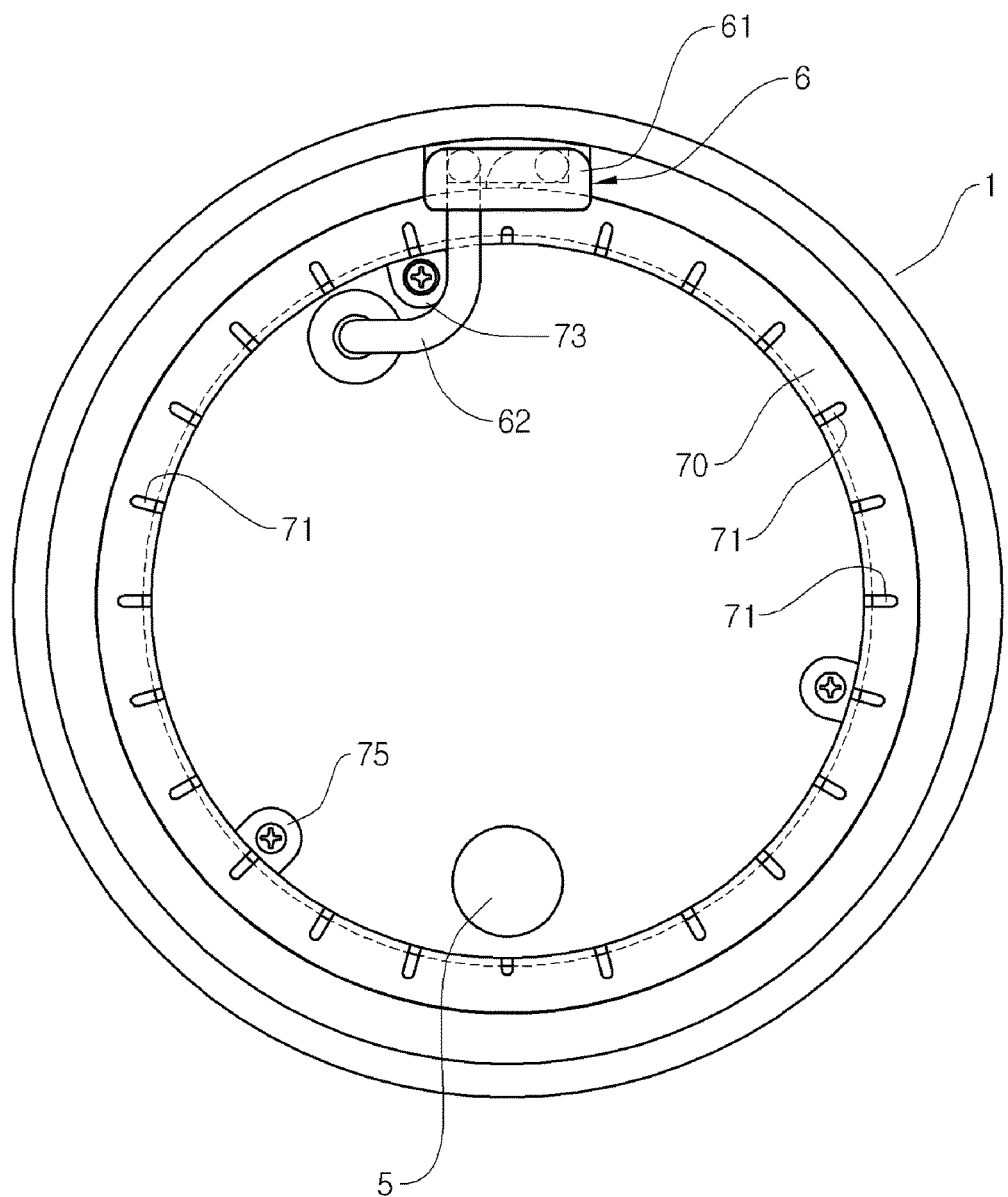

[Fig. 4]
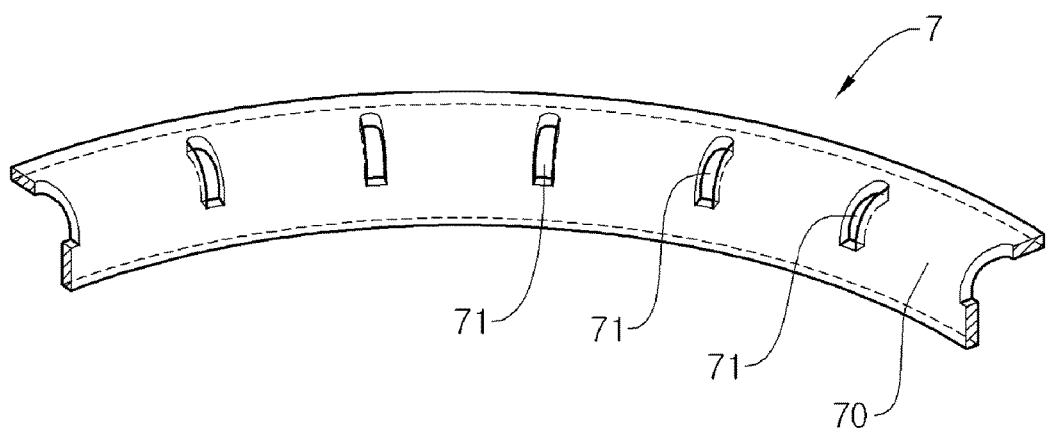

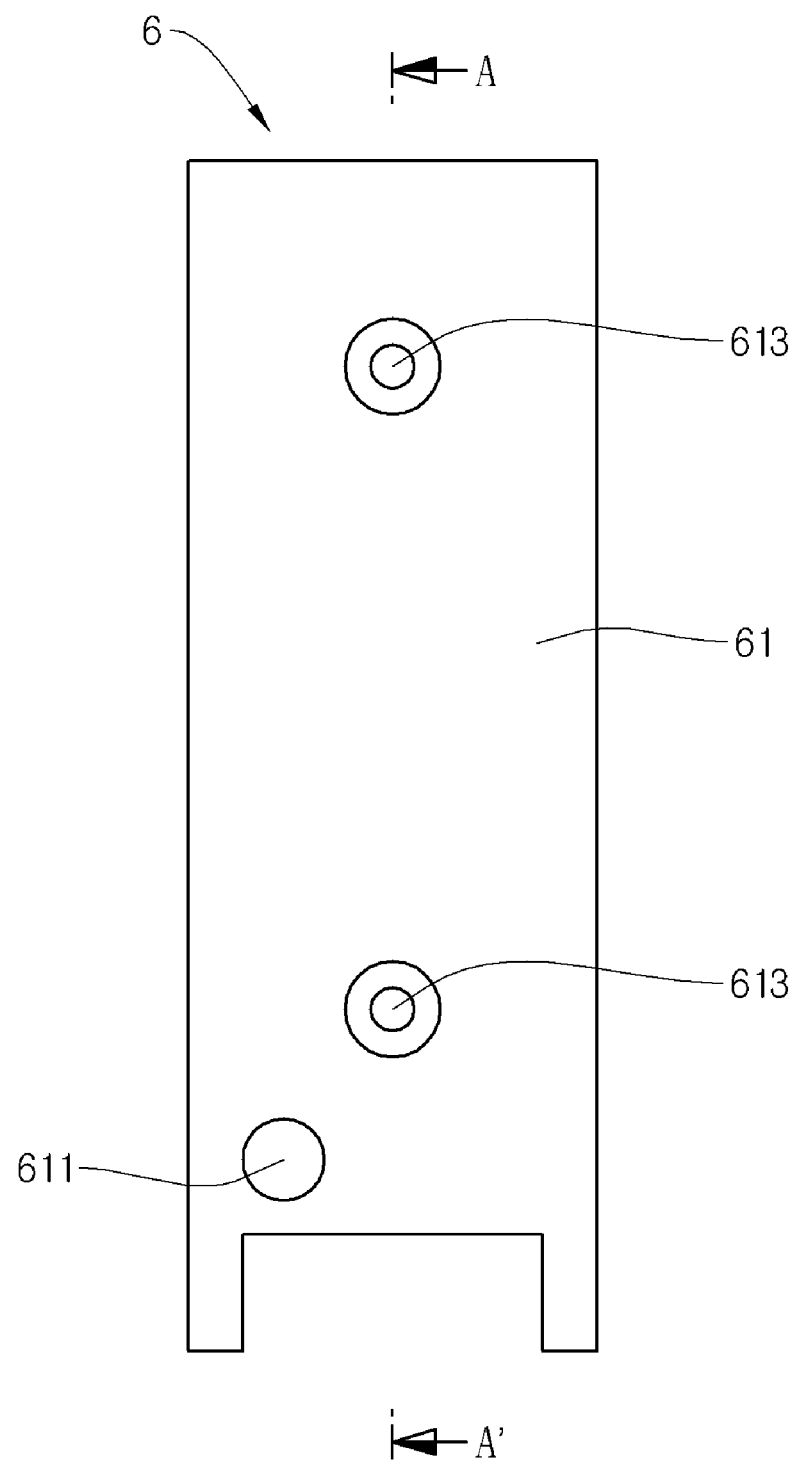
[Fig. 5a]

[Fig. 5b]
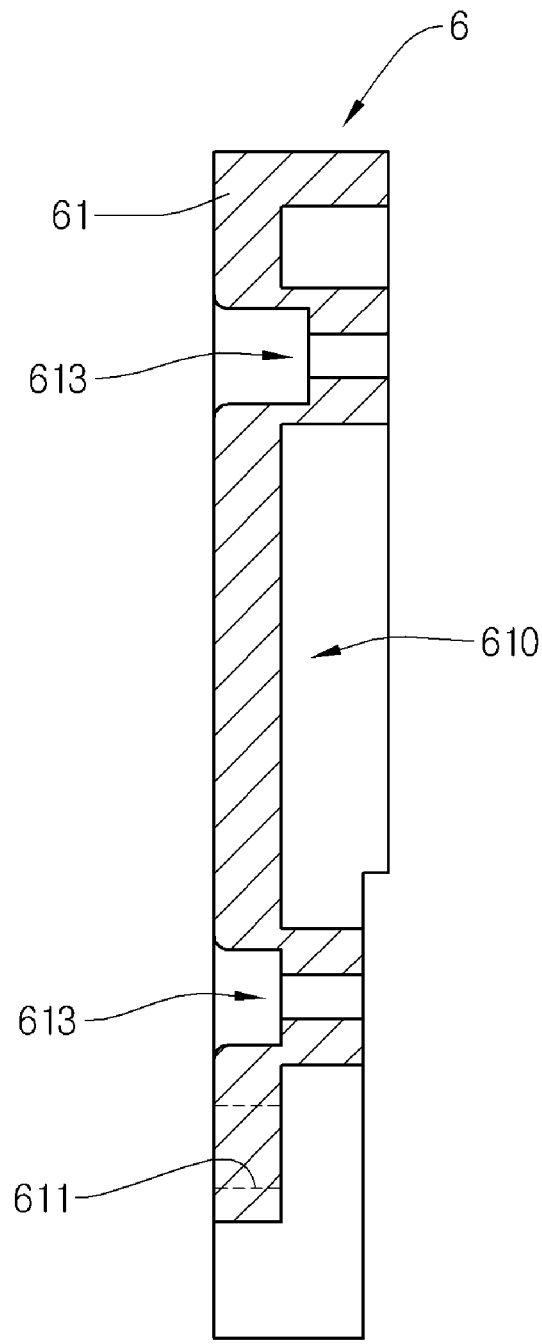

[Fig. 5c]
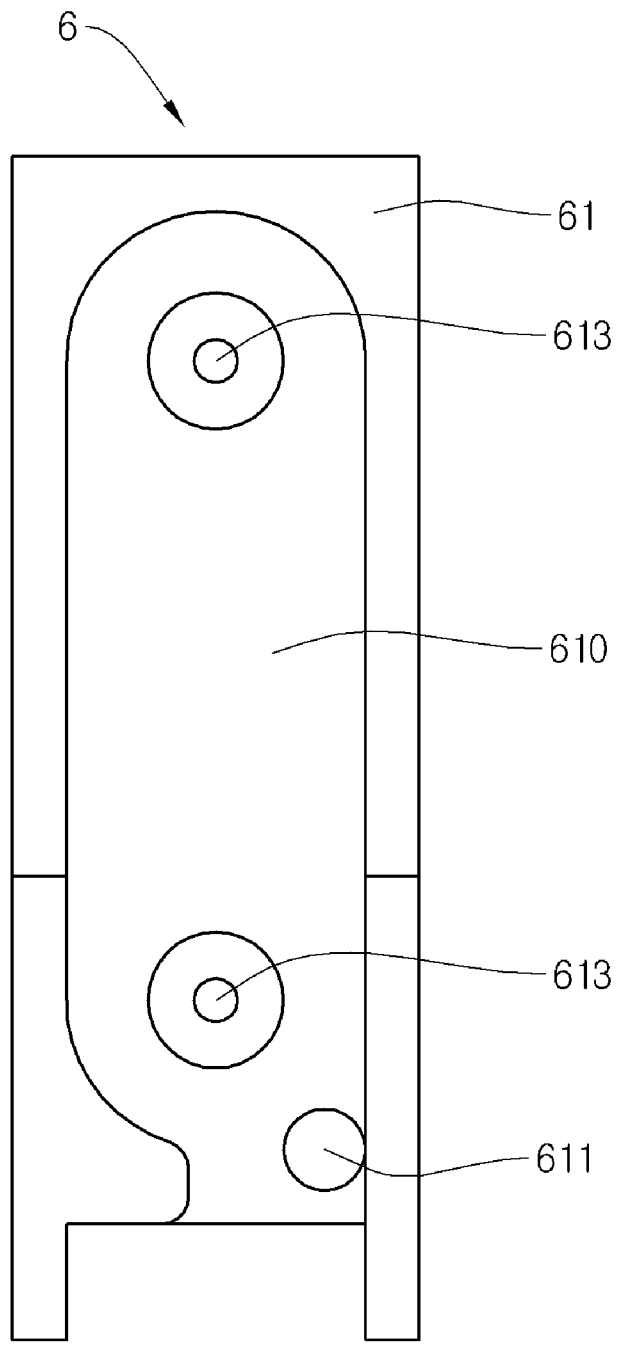

[Fig. 6]
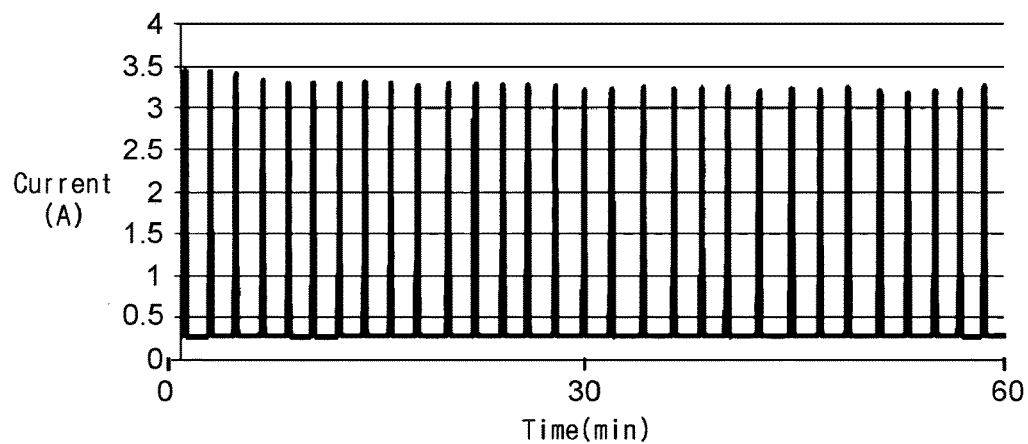
[Fig. 7a]
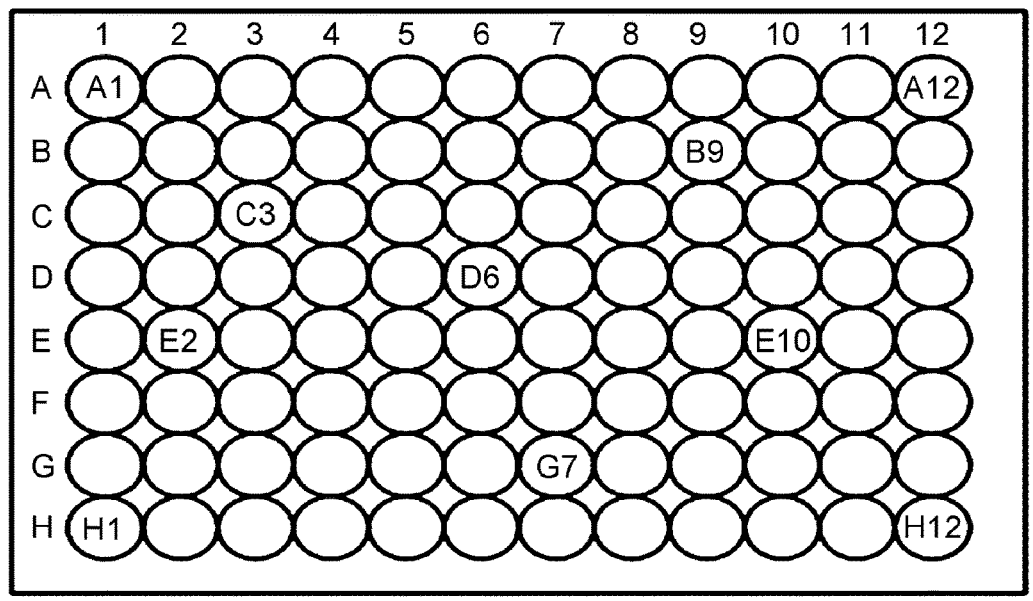

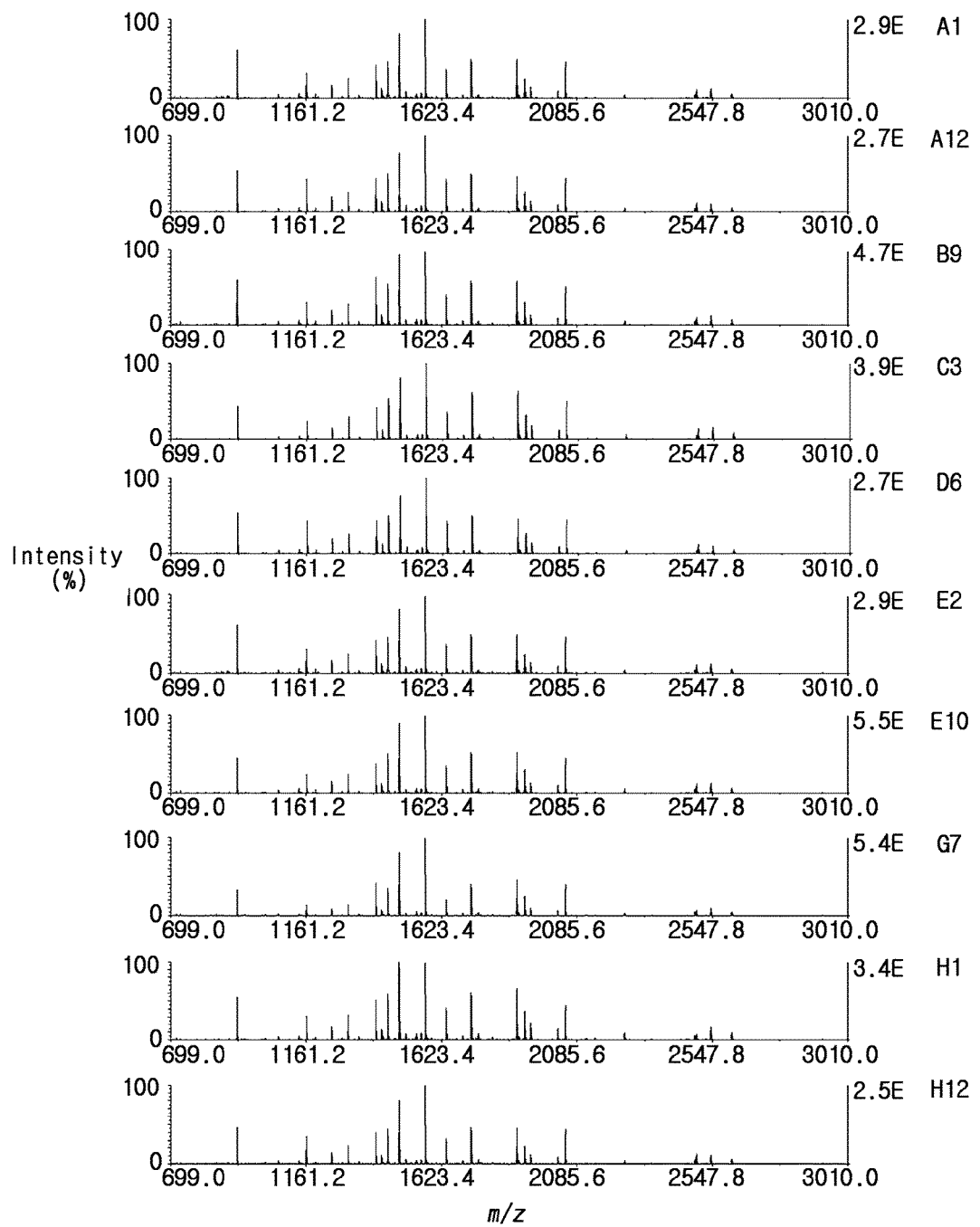
[Fig. 7b]

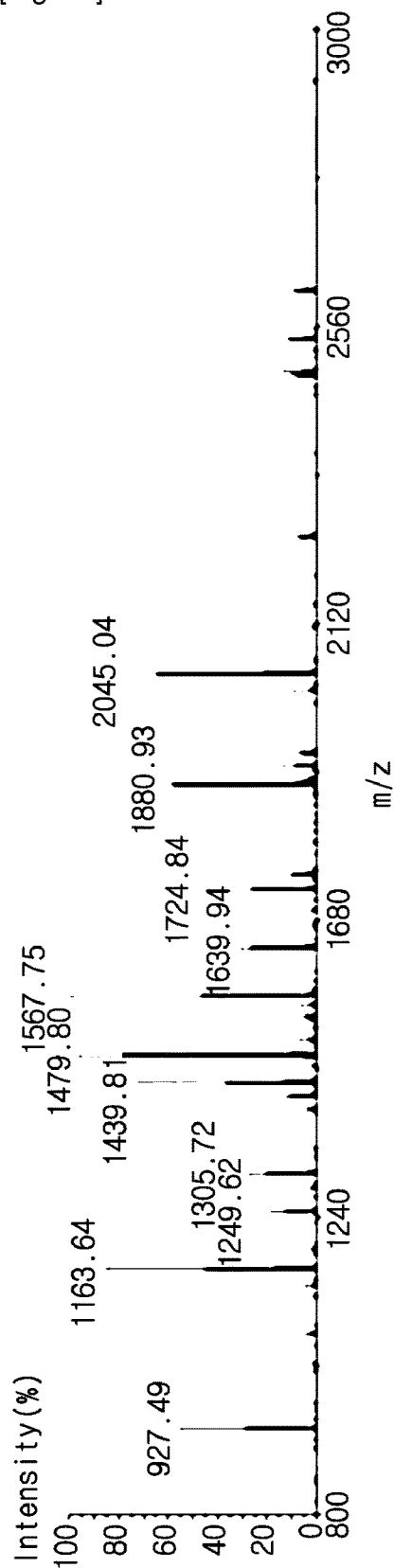
[Fig. 8a]

[Fig. 8b]
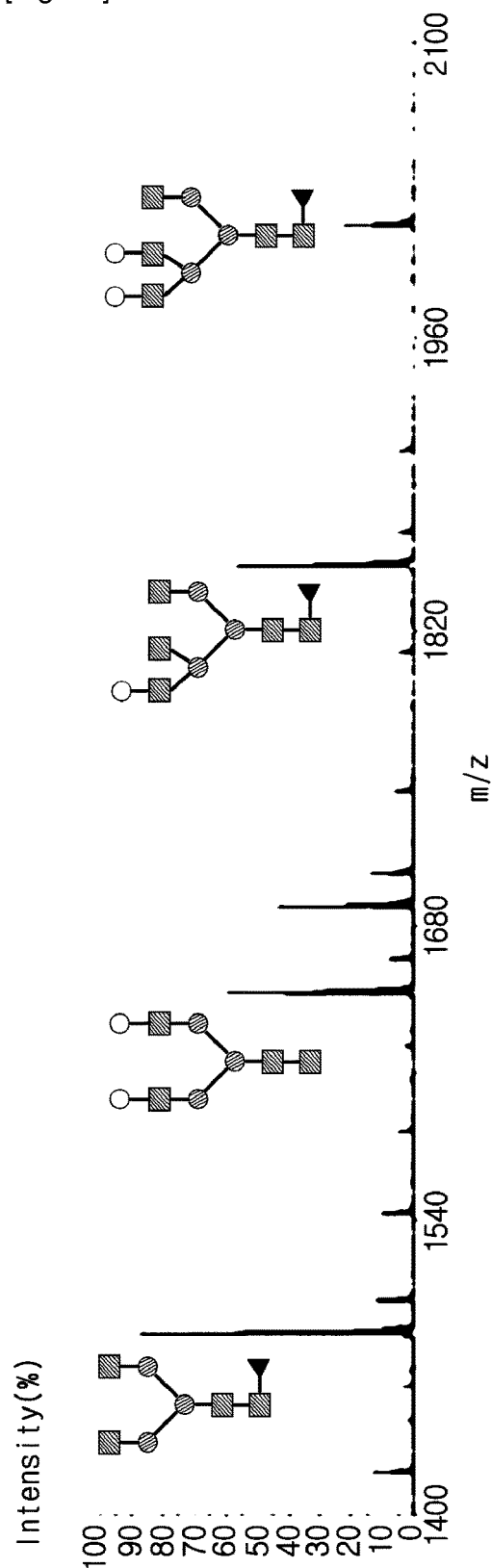

[Fig. 8c]
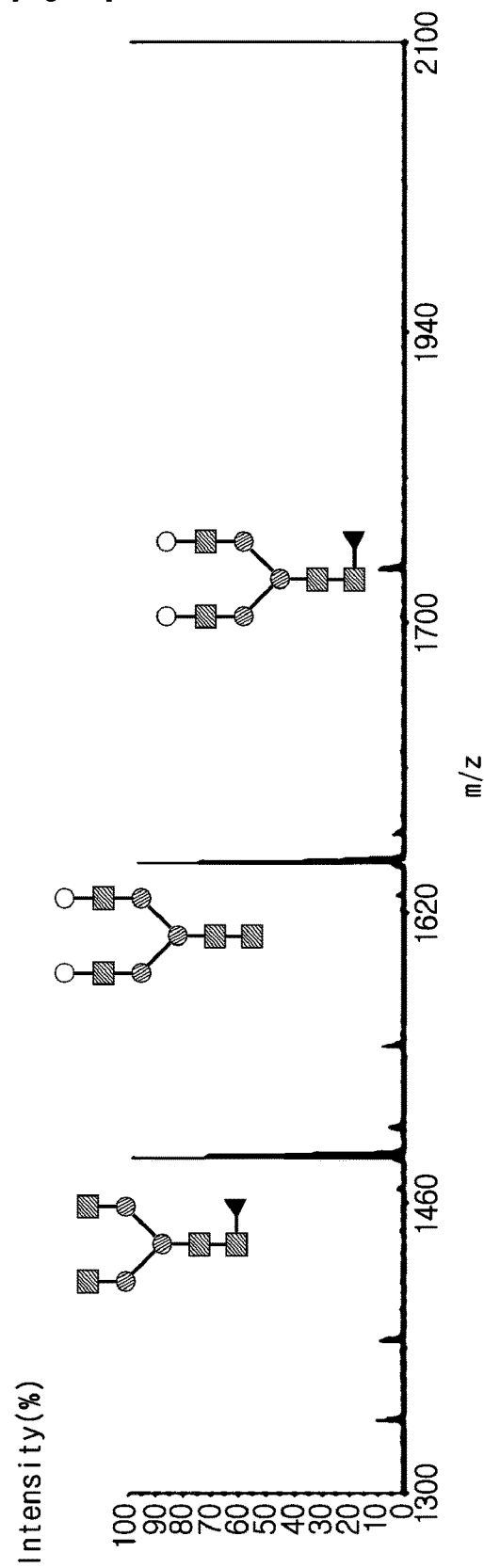

APPARATUS AND METHOD FOR PROCESSING A SAMPLE USING MICROWAVE

TECHNICAL FIELD

Embodiments relate to an apparatus and a method for processing a sample using microwaves.

BACKGROUND ART

Enzymes are a kind of protein composed of multiple amino acids connected to each other that catalyze (=increase rate of) chemical reaction. Most of the proteins have 3-dimensional structures and can be changed depending on many factors. Among them, temperature change is one of most important factor. And many enzymatic reactions (enzymatic digestion) occur at temperatures similar to the body temperature. Trypsin is an enzyme that cleaves lysine or arginine chains of proteins. Trypsin digestion can be used for breaking them down into peptides and analyzing the resulting peptide fragments. Typically, such enzymatic reactions require about 12 or more hours of time at about 37° C.

If the enzymatic reactions are performed while irradiating microwaves, the proteolytic cleavage may be accelerated. For example, Korean Patent Application Publication No. 10-2009-0110599 describes heating and ionic conduction based on dipolar polarization using microwaves and discloses bonding or cleavage of specific compounds using the same. And, a microwave oven, which is a commonly used kitchen appliance, heats food by heating water molecules with electromagnetic waves of resonance frequency.

Since the microwave oven is a kind of cavity resonator enclosed with metal, there are locations where the electromagnetic waves are stronger and weaker inside the microwave oven. In order that the microwaves are uniformly absorbed by food, mixing of the irradiated microwaves or rotating of the food container is required. Not just the microwave oven, all research-purpose microwave instruments have the same problem that the microwaves do not reach all locations uniformly. In addition, an apparatus for conducting enzymatic reactions using microwaves has the problem that the generation of microwaves is stopped instantly when the temperature inside a chamber reaches a setting temperature. This inevitably slows the enzymatic reactions.

DISCLOSURE OF INVENTION

Technical Problem

In accordance with an aspect of the present disclosure, an apparatus and a method for processing a sample using microwaves may be provided, which is capable of uniformly controlling the temperature of different locations in a chamber by inducing a bubbling effect by supplying a gas to a refrigerant.

Solution to Problem

An apparatus for processing a sample using microwaves according to an embodiment comprises: a reaction vessel comprising a chamber which accommodates a refrigerant and a sample and an injection port through which a gas is injected; a microwave source which irradiates microwaves into the chamber; a connector which carries the gas injected through the injection port; and a gas supplier which is located in the chamber and injects the gas carried by the connector to a refrigerant in the chamber.

In the apparatus, the connector may comprise a gas carrying portion located above a level of the refrigerant in the chamber.

A method for processing a sample using microwaves according to an embodiment comprises: placing a refrigerant and a sample inside a chamber of a reaction vessel; irradiating microwaves into the chamber; injecting a gas into the reaction vessel while the microwaves are irradiated into the chamber; carrying the injected gas through a connector; and injecting the gas carried through the connector to the refrigerant in the chamber. The connector may comprise a gas carrying portion located above a level of the refrigerant in the chamber.

Advantageous Effects of Invention

By the apparatus and method for processing a sample using microwaves according to an aspect of the present disclosure, through a bubbling effect generated by supplying a gas to a refrigerant in a chamber, the upper and lower layers as well as middle and side portions of the refrigerant can be circulated uniformly. As a result, the inside of the chamber can be heated uniformly and a large amount of sample can be processed at once. Since homogeneous microwaves can be outputted continuously, sample processing such as enzymatic reactions can be achieved in very short time as compared to the conventional methods.

BRIEF DESCRIPTION OF DRAWINGS

FIG. 1 schematically shows an apparatus for processing a sample using microwaves according to an embodiment.

FIG. 2 is a cross-sectional view of a reaction vessel in an apparatus for processing a sample using microwaves according to an embodiment.

FIG. 3 is a plan view of a reaction vessel in an apparatus for processing a sample using microwaves according to an embodiment.

FIG. 4 is a partial perspective view of a gas supplier in an apparatus for processing a sample using microwaves according to an embodiment.

FIG. 5a is a front view of a connector in an apparatus for processing a sample using microwaves according to an embodiment.

FIG. 5b is a side cross-sectional view along the line A-A' is FIG. 5a.

FIG. 5c is a rear view of the connector shown in FIG. 5a.

FIG. 6 shows output microwaves with time after a setting temperature is reached in an apparatus for processing a sample using microwaves according to an embodiment.

FIG. 7a schematically shows measurement locations on a 96-well plate.

FIG. 7b shows a result of performing enzymatic reaction using an apparatus for processing a sample using microwaves according to an embodiment at the measurement locations shown in FIG. 7a.

FIGS. 8a to 8c show results of performing enzymatic reaction using an apparatus for processing a sample using microwaves according to embodiments.

MODE FOR THE INVENTION

Hereinafter, the embodiments of the present disclosure will be described in detail with reference to accompanying drawings.

FIG. 1 schematically shows an apparatus for processing a sample using microwaves according to an embodiment.

Referring to FIG. 1, an apparatus for processing a sample using microwaves may comprise a reaction vessel 1 and a microwave source 2. The microwave source 2 may comprise a device capable of generating microwaves, such as a magnetron. When the microwaves irradiated from the microwave source 2 reach the reaction vessel 1 along a predetermined path, the microwaves may heat a sample located inside a chamber (not shown) of the reaction vessel 1. For example, the microwaves may aid in enzymatic reaction (digestion) of proteins into peptides.

Further, the apparatus for processing a sample using microwaves may comprise a controller 4 and a temperature sensor 5. The temperature sensor 5 is a device for measuring the temperature inside the chamber of the reaction vessel 1. The temperature sensor 5 may be, for example, a thermocouple sensor, but is not limited thereto. The controller 4 may maintain the temperature inside the chamber of the reaction vessel 1 at a predetermined setting temperature by controlling the microwave source 2 based on the temperature measured by the temperature sensor 5. For example, the controller 4 may operate to maintain the temperature inside the chamber of the reaction vessel 1 at 37° C., close to the body temperature. The controller 4 may compare the setting temperature with the temperature measured by the temperature sensor 5 and control irradiation of microwaves by the microwave source 2 such that the difference between the setting temperature and the measured temperature is not greater than a threshold value, for example, 0.1° C. However, in other embodiments, the setting temperature and the threshold value may be determined appropriately without being limited to the aforesaid example.

In addition, the apparatus for processing a sample using microwaves may further comprise a pump 3 for injecting a gas to the reaction vessel 1. Inside the chamber of the reaction vessel 1, the sample and a refrigerant are accommodated together. By injecting a gas to the refrigerant using the pump 3, bubbles may be formed in the refrigerant. As a result, through a bubbling effect generated by the bubbles, the refrigerant may be circulated uniformly in the chamber and thus uniformly heat the inside of the chamber. For example, the refrigerant in the chamber may be water and the gas injected by the pump 3 may be air. However, in other embodiments, different refrigerant or gas may also be used.

FIG. 2 is a cross-sectional view of a reaction vessel in an apparatus for processing a sample using microwaves according to an embodiment.

Referring to FIG. 2, an apparatus for processing a sample using microwaves may comprise a reaction vessel 1, a connector 6 and a gas supplier 7. The reaction vessel 1 may comprise a chamber 10 and an injection port 13. The chamber 10 provides a space for accommodating a refrigerant and a sample. The gas to be supplied to the refrigerant is injected into the reaction vessel 1 through the injection port 13. The reaction vessel 1 may be formed of a material through which microwaves can penetrate. For example, the reaction vessel 1 may be formed of a perfluoroalkoxy (PFA) material such as Teflon, but is not limited thereto. Further, the inside of the chamber 10 may be coated with, for example, a fluorocarbon material. However, this is only exemplary, and the chamber 10 may be coated with different materials or may not be coated.

In an embodiment, the chamber 10 may comprise a first compartment 101 and a second compartment 102. The first compartment 101 is a space for accommodating the refrigerant and may have a first diameter $R_1$. For example, the first compartment 101 may be formed to have a diameter and a depth for accommodating about 500 mL of refrigerant, but is not limited thereto. The refrigerant may be filled in the entire space of the first compartment 101. Alternatively, the refrigerant may be filled only partly in the space of the first compartment 101. For example, in the first compartment 101, the space for accommodating the refrigerant may be divided, for example, by a groove formed on the side wall of the reaction vessel 1.

The second compartment 102 is a space for accommodating the sample and may have a second diameter $R_2$ which is different from the first diameter $R_1$. For example, the second diameter $R_2$ of the second compartment 102 may be larger than the first diameter $R_1$ of the first compartment 101. The sample may be located in the chamber 10 using a step structure between the first compartment 101 and the second compartment 102 formed as a result of the difference in diameter. For example, the sample may be injected into a plurality of wells of a well plate, which are formed as an array, and the well plate may be located between the first compartment 101 and the second compartment 102.

The injection port 13 of the reaction vessel 1 is for injecting a gas into the reaction vessel 1. The injection port 13 may be connected, for example, to the pump 3 described referring to FIG. 1. Also, a connecting member (not shown) to facilitate the connection of a tube for gas injection may be coupled with the injection port 13. In FIG. 2, the center portion of the bottom surface of the reaction vessel 1 on which the injection port 13 is located is indented. However, this is only exemplary, and the injection port 13 may be located on the other surfaces of the reaction vessel 1.

The connector 6 is for carrying the gas injected through the injection port 13 to the gas supplier 7. The connector 6 may comprise a connector body 61 and a tube 62. The connector body 61 forms a path through which the tube 62 can pass and may comprise at least one hole or groove through which the tube 62 can be inserted. Details about the connector body 61 will be described later referring to FIGS. 5a to 5c. The connector body 61 may be formed of polyacetal, but is not limited thereto. The tube 62 may be connected to the injection port 13, and the gas injected through the injection port 13 may be carried along the tube 62 and to the gas supplier 7.

The connector 6 may at least partially include a gas carrying portion which is located above the level of the refrigerant in the chamber 10. For example, if the refrigerant is filled in the first compartment 101 of the chamber 10, the distance $D_1$ from the bottom surface of the chamber 10 to a portion of the tube 62 of the connector 6 may be larger than the depth $D_2$ of the first compartment 101. However, the refrigerant may be filled up to a different height in the chamber 10. Also in this case, the connector 6 may be disposed to at least partially include a portion where the tube 62 is located above the level of the refrigerant.

The tube 62 is for carrying a gas by the gas supplier 7 so as to inject the gas to the refrigerant. The tube 62 is connected such that material exchange with the refrigerant is possible. While the gas is injected through the tube 62, the refrigerant is not flown into the tube 62 because of gas pressure. However, while the gas is not injected, the refrigerant may be reversely flown into the tube 62 because of the pressure of the refrigerant itself. However, since at least a portion of the tube 62 is located above the level of the refrigerant, even when the refrigerant is flown into the tube 62, the refrigerant is filled only up to the level of the whole injected refrigerant in the chamber 10 but cannot completely pass through the connector 6. Accordingly, leakage of the refrigerant out of the chamber 10 may be prevented.

FIG. 3 is a plan view of a reaction vessel in an apparatus for processing a sample using microwaves according to an embodiment, and FIG. 4 is a partial perspective view of a gas supplier in an apparatus for processing a sample using microwaves according to an embodiment.

Referring to FIGS. 3 and 4, a gas supplier 7 is for supplying a gas carried by a connector 6 to a refrigerant. The gas supplier 7 may be located inside a chamber 10. The gas supplier 7 may be located inside a first compartment 101 of the chamber 10 wherein a refrigerant is accommodated. The gas supplier 7 may also be located on the bottom surface of the chamber 10. Further, the gas supplier 7 may be formed with a shape of a closed curve extending along the inner periphery of the chamber 10. For example, if the chamber 10 has a cylindrical shape, the gas supplier 7 may have a shape of a hollow ring. The gas supplier 7 may be formed at least partly of polyacetal, but is not limited thereto.

The gas supplier 7 may comprise at least one hole 71 for injecting gas. For example, the gas supplier 7 may comprise a cover 70 extending along the inner wall of the chamber 10. The cover 70 may have a bent or curved shape such that a space is formed between the cover 70 and the inner wall of the chamber 10. A gas may be injected into the space between the cover 70 and the inner wall of the chamber 10. The at least one hole 71 may be a plurality of holes arranged on the cover 70 with regular intervals. The gas supplier 7 may be connected to the connector 6 such that gas exchange is possible, so as to inject the gas into the gas supplier 7. The gas injected into the gas supplier 7 may be supplied to the refrigerant through the at least one hole 71.

The gas supplier 7 may comprise at least one fixing unit 73. The fixing unit 73 is a means for fixing the gas supplier 7 to a reaction vessel 1 using a fixing member such as a screw. For example, the gas supplier 7 may be fixed on the bottom surface of the chamber 10 in the reaction vessel 1 using the fixing unit 73. However, this is only exemplary, and the gas supplier 7 may comprise a different fixing means or no different fixing means in other embodiments.

FIGS. 2 to 4 are drawings for describing the functions of the respective components of the apparatuses for processing a sample using microwaves according to the embodiments. Those skilled in the art will appreciate that the specific locations and dimensions of the components shown in the drawings may not necessarily be the same as shown in the drawings and the locations and dimensions of the components may not necessarily be the actual locations and dimensions.

FIG. 5a is a front view of a connector in an apparatus for processing a sample using microwaves according to an embodiment, FIG. 5b is a side cross-sectional view along the line A-A' is FIG. 5a, and FIG. 5c is a rear view of the connector shown in FIG. 5a.

Referring to FIGS. 5a to 5c, a connector body 61 of a connector 6 may comprise a groove 610 and a hole 611 to which a tube (not shown) carrying a gas can be inserted. The connector body 61 may comprise at least one fixing unit 613 for fixing the connector 6 to a reaction vessel using a fixing member such as a screw. The tube may be inserted to the groove 610 of the connector body 61 through the hole 611, and the inserted tube may extend in the groove 610 while enclosing the at least one fixing unit 613 and may come out of the connector body 61.

The location of the at least one fixing unit 613 may be determined adequately considering the structure of a chamber and the level of a refrigerant that will be accommodated in the chamber, such that a portion of the tube extending along the outside of the fixing unit 613 is located above the level of the refrigerant in the chamber. By adequately disposing the connector 6 having such configuration in the chamber, at least a portion of the tube of the connector 6 may be located above the level of the refrigerant, as described above referring to FIG. 2.

FIG. 6 shows output microwaves with time after a setting temperature is reached according to an embodiment. FIG. 6 shows change in output microwaves with time after the temperature inside a chamber of a reaction vessel reaches a setting temperature of 37° C. using a microwave source outputting microwaves of about 400 W. As illustrated, microwaves are output very uniformly and stably for one hour after the setting temperature is reached.

FIG. 7a schematically shows measurement locations on a well plate to which a sample is injected. Referring to FIG. 7a, on about 130 mm× about 85 mm sized 96-well plate with 96 wells arranged as an array of 12 rows (rows 1 to 12) and 8 columns (columns A to H), 10 measurement locations (A1, A12, B9, C3, D6, E2, E10, G7, H1 and H12) were randomly selected. FIG. 7b shows a result of performing enzymatic reaction using an apparatus for processing a sample using microwaves according to an embodiment at the measurement locations shown in FIG. 7a. It can be seen that the reaction is not substantially affected by the locations. In the apparatus for processing a sample, water was used as a refrigerant and air was supplied as a gas for a bubbling effect.

Specifically, the enzymatic reaction was performed after placing the 96-well plate inside a chamber of a reaction vessel while irradiating microwaves of about 400 W, with a setting temperature set at 37° C. By analyzing the product of the enzymatic reaction by matrix-assisted laser desorption/ionization time-of-flight (MALDI-TOF) mass spectrometry, signal intensities with respect to mass-to-charge ratio (m/z) were obtained as shown in FIG. 7b. Since the wells of the 96-well plate are uniformly heated due to bubbling effect, the enzymatic reaction could be achieved uniformly with little effect from the measurement location.

FIGS. 8a to 8c show results of performing enzymatic reaction using an apparatus for processing a sample using microwaves according to embodiments. The product of the enzymatic reaction was analyzed by MALDI-TOF mass spectrometry in order to identify the peptides cleaved by the enzymatic reaction. In the apparatus for processing a sample, water was used as a refrigerant and air was supplied as a gas for providing a bubbling effect.

FIG. 8a shows an enzymatic reaction result using a sample prepared by placing about 85 µL of 1 nmol bovine serum albumin (BSA) at about 95° C. for about 20 minutes, performing reaction at about 50° C. for about 15 minutes after adding about 1 µL of about 45 mM dithiothreitol (DTT, pH about 7.9), and then performing reaction at about 25° C. for about 15 minutes after adding about 1 µL of about 100 mM iodoacetamide. The prepared sample was mixed with trypsin and placed in a chamber of a reaction vessel. Then, enzymatic reaction was performed by irradiating microwaves of about 400 W for about 10 minutes.

FIG. 8b shows an enzymatic reaction result using a sample prepared by mixing about 50 µL of serum with about 50 µL of buffer. The prepared sample was mixed with PNGase F and placed in a chamber of a reaction vessel. Then, enzymatic reaction was performed by irradiating microwaves of about 400 W for about 10 minutes, with the setting temperature set at 37° C. After the enzymatic reaction, the cleaved sugar chains were separated and purified using a graphitized carbon column. The purified neutral glycan was subjected to MALDI-TOF analysis using 2,5-dihydroxybenzoic acid (DHB) as a matrix. FIG. 8c shows a result of performing PNGase F enzymatic reaction using a sample prepared by the same method as shown in FIG. 8b.

In FIGS. 8b and 8c, the glycan structures of the corresponding mass-to-charge ratio peaks are shown on the left or above the peaks. In the structures shown,  represents mannose (Man), ◯ represents hexose (Hex),  represents N-acetylglucosamine (GlcNAc), and  represents fucose (Fuc).

As seen from FIGS. 8a to 8c, the samples could be identified by performing enzymatic reaction for about 10 minutes using the apparatus for processing a sample using microwaves according to the embodiments. Considering that about 16 hours is required to perform enzymatic reaction using a sample prepared by mixing about 50 μL of serum and about 50 μL of buffer with a conventional microwave apparatus, the apparatus for processing a sample using microwaves according to the embodiments of the present disclosure is advantageous in that it can process a large amount of sample in very short time.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

INDUSTRIAL APPLICABILITY

Embodiments relate to an apparatus and a method for processing a sample using microwaves.

The invention claimed is:

1. An apparatus for processing a sample using microwaves comprising:
    a reaction vessel comprising a chamber which accommodates a liquid refrigerant and a sample and an injection port formed on a bottom surface of the reaction vessel, wherein a gas is injected into the reaction vessel from outside through the injection port, wherein the liquid refrigerant fills the chamber up to a height;
    a microwave source which irradiates microwaves into the chamber;
    a connector which receives the gas injected through the injection port and carries the gas injected through the injection port; and
    a gas supplier which is located in the chamber, wherein the gas supplier receives the gas carried by the connector and supplies the gas carried by the connector into the liquid refrigerant that fills the chamber up to the height, to form gas bubbles in the liquid refrigerant and circulate the refrigerant in the chamber,
    wherein the connector comprises a gas carrying portion located above the height of the liquid refrigerant in the chamber, and another portion located below the height of the refrigerant in the chamber and connected between the gas carrying portion and the gas supplier, wherein the gas supplier is located on a bottom surface of the chamber, and
    wherein the connector further comprises a tube, wherein both ends of the tube are communicatively coupled to the injection port and the gas supplier, respectively, so as to enable gas exchange, and wherein the gas carrying portion is a portion of the tube.

2. The apparatus according to claim 1, wherein the gas supplier is extended along an inner periphery of the chamber and comprises at least one hole for injecting the gas.

3. The apparatus according to claim 1, wherein the chamber comprises:
    a first compartment having a first diameter and accommodating the liquid refrigerant; and
    a second compartment having a second diameter which is larger than the first diameter.

4. The apparatus according to claim 3, further comprising a well plate disposed in the chamber using a step structure between the first compartment and the second compartment, wherein the well plate comprises a plurality of wells configured to accommodate the sample.

5. The apparatus according to claim 1, wherein the reaction vessel comprises perfluoroalkoxy.

6. A method for processing a sample using microwaves, comprising:
    placing a liquid refrigerant and a sample inside a chamber of a reaction vessel so that the liquid refrigerant fills the chamber up to a height;
    irradiating microwaves into the chamber;
    injecting a gas from outside into the reaction vessel through an injection port formed on a bottom surface of the reaction vessel while the microwaves are irradiated into the chamber;
    carrying the gas injected through the injection port using a connector; and
    injecting, by a gas supplier connected to the connector and located on the bottom surface of the chamber, the gas carried through the connector to the liquid refrigerant that fills the chamber up to the height, to form gas bubbles in the liquid refrigerant and circulate the refrigerant in the chamber,
    wherein the connector comprises a gas carrying portion located above the height of the refrigerant in the chamber, and another portion located below the height of the refrigerant in the chamber and connected between the gas carrying portion and the gas supplier, and
    wherein the connector further comprises a tube, wherein both ends of the tube are communicatively coupled to the injection port and the gas supplier, respectively, so as to enable gas exchange, and wherein the gas carrying portion is a portion of the tube.

7. The method according to claim 6, wherein said injecting the gas to the refrigerant in the chamber comprises injecting the gas to the refrigerant through at least one hole arranged along an inner periphery of the chamber.

8. The apparatus of claim 1, wherein the gas is injected from the outside into the injection port formed on the bottom surface of the reaction vessel, carried through the connector including the gas carrying portion located above the height of the liquid refrigerant in the chamber, and is received by the gas supplier located on the bottom surface of the chamber to supply the gas to the liquid refrigerant.

* * * * *